US00PP31952P2

(12) United States Plant Patent
Bryant

(10) Patent No.: US PP31,952 P2
(45) Date of Patent: Jul. 7, 2020

(54) ALOE PLANT NAMED 'BAGCO01'

(50) Latin Name: ***Aloe* x *humilis***
Varietal Denomination: 'BAGCO01'

(71) Applicant: Austin Bryant, Zolfo Spring, FL (US)

(72) Inventor: Austin Bryant, Zolfo Spring, FL (US)

(73) Assignee: Bryant Ag-Co, LLC, Zolfo Springs, FL (US)

( * ) Notice: Subject to any disclaimer, the term of this patent is extended or adjusted under 35 U.S.C. 154(b) by 0 days.

(21) Appl. No.: 16/602,315

(22) Filed: Sep. 13, 2019

(51) Int. Cl.
*A01H 5/12* (2018.01)

(52) U.S. Cl.
USPC ..... Plt./373

(58) Field of Classification Search
USPC ..... Plt./373
CPC ..... A01H 5/12
See application file for complete search history.

*Primary Examiner* — Annette H Para
(74) *Attorney, Agent, or Firm* — James R. Holm

(57) ABSTRACT

A new and distinct *Aloe* plant named 'BAGCO01' particularly distinguished by a dwarf growth habit and unique light greenish-yellow foliage coloration in the center of the rosette, is disclosed.

3 Drawing Sheets

Figure 1:
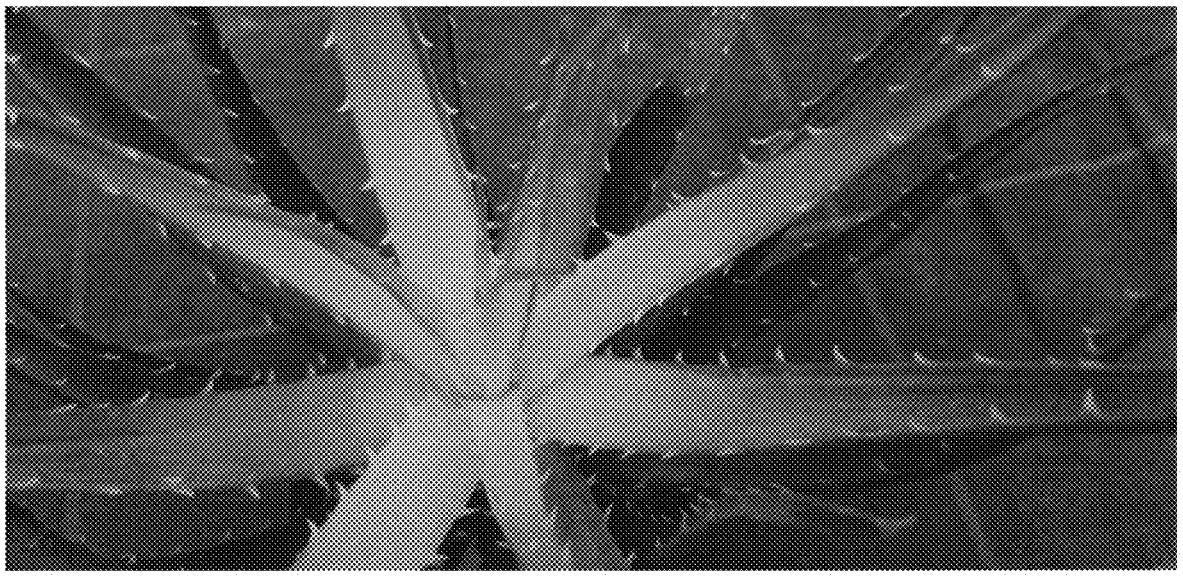

Genus and species: *Aloe* x *humilis.*
Variety denomination: 'BAGCO01'.

BACKGROUND OF THE INVENTION

The present invention comprises a new and distinct variety of *Aloe* plant, botanically known as *Aloe* x *humilis*, and hereinafter referred to by the variety name 'BAGCO01'. This new *Aloe* plant was discovered by the inventor as a single branch mutation from an unnamed progenitor *Aloe* x *humilis* plant derived from in-vitro meristem tip culture. The discovery of the new plant was made by the inventor in January 2015 in a non-publically accessible area of a commercial greenhouse located in Zolfo Springs, Fla. The inventor harvested the original single branch mutation based on its unique, symmetrical and uniform light greenish-yellow leaf coloration in the center of the rosette, planted said mutation as a single plant in a container and grew the plant out for subsequent evaluation and asexual reproduction. The inventor harvested and planted basal branches that grew from the single branch mutation to establish a second generation of plants. A third generation of plants was established from planting basal branches that the inventor harvested from the second generation of plants. The inventor repeated harvesting, planting and growing several generations of plants and determined that 'BAGCO01' retained its unique, symmetrically uniform light-greenish yellow leaf coloration in the center of the rosette. 'BAGCO01' has been asexually reproduced repeatedly by in-vitro meristem tip cuttings in a tissue culture lab in Zolfo Springs, Fla. and has been found to retain its distinctive characteristics and reproduce true-to-type through 4 generations of in-vitro asexual propagation.

Plant Breeder's Rights for this variety have not been applied for. 'BAGCO01' has not been made publicly available or sold anywhere in the world prior to the effective filing date of this application.

SUMMARY OF THE INVENTION

The new *Aloe* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Aloe* variety when grown under normal horticultural practices in Zolfo Springs, Fla. The combination of these characteristics distinguishes 'BAGCO01' as a new and distinct variety of *Aloe:*

1. Dwarf growth habit; and
2. Unique light greenish-yellow foliage coloration in the center of the rosette.

DESCRIPTION OF THE PHOTOGRAPHS

This new *Aloe* plant is illustrated by the accompanying photographs which show the overall plant habit including foliage of the plant. The colors shown are as true as can be reasonably obtained by conventional photographic procedures. The photographs are of approximately 6-month-old plants grown in 4-inch round (1-pint) containers in Zolfo Springs, Fla. The photographs were taken in July 2019 in Florida under natural light. Colors in the photographs may differ slightly from the color values cited in the botanical description which accurately describes the colors of the new variety.

Figure 2:
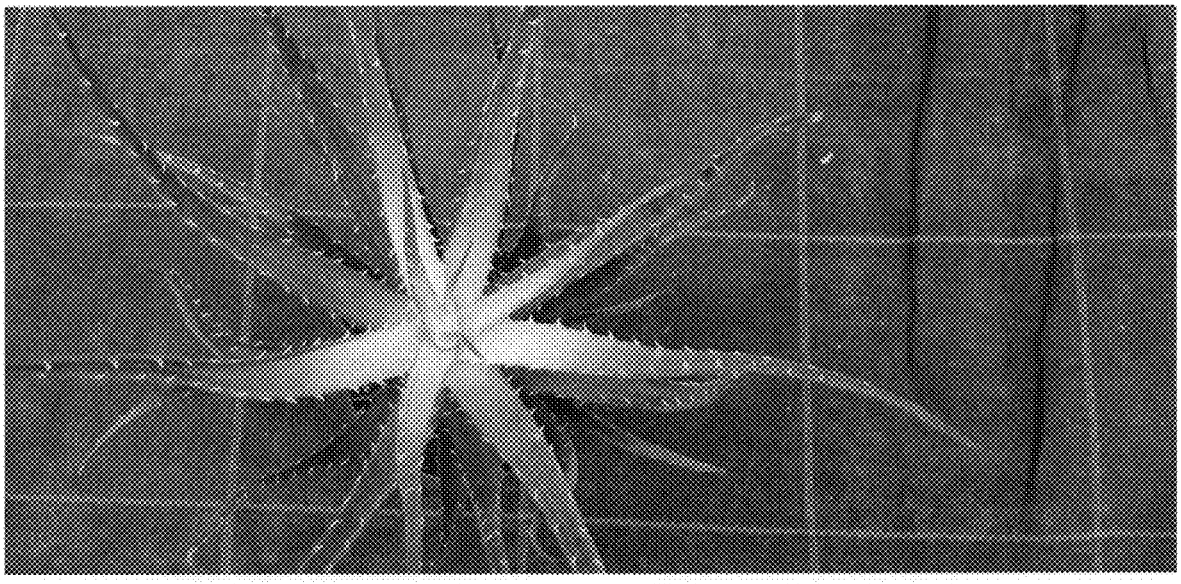

FIG. 1 and FIG. 2 show top views of the central rosette of a typical plant of 'BAGCO01'.

Figure 3:
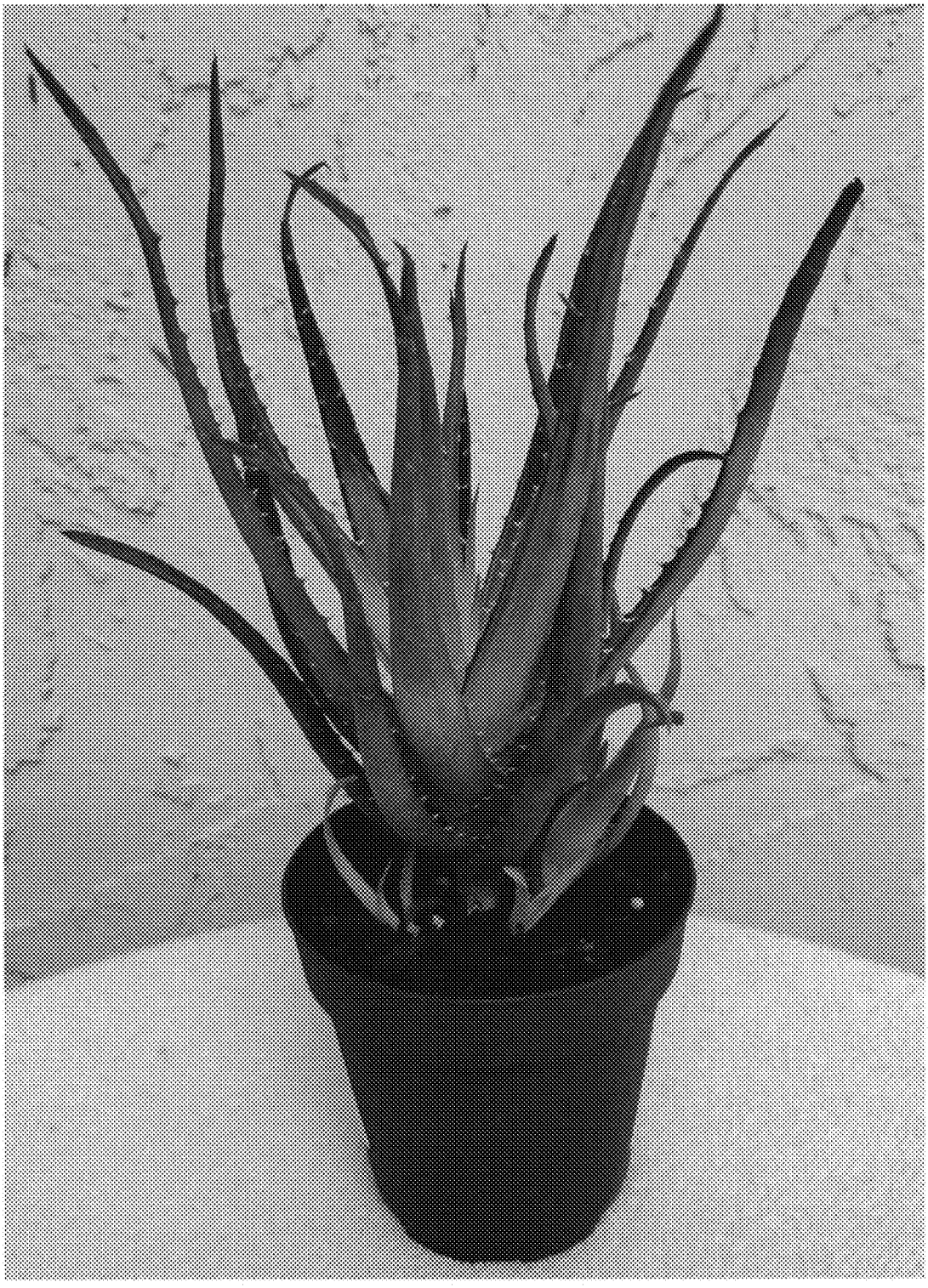

FIG. 3. shows a side view of a typical plant of 'BAGCO01'.

Figure 4:
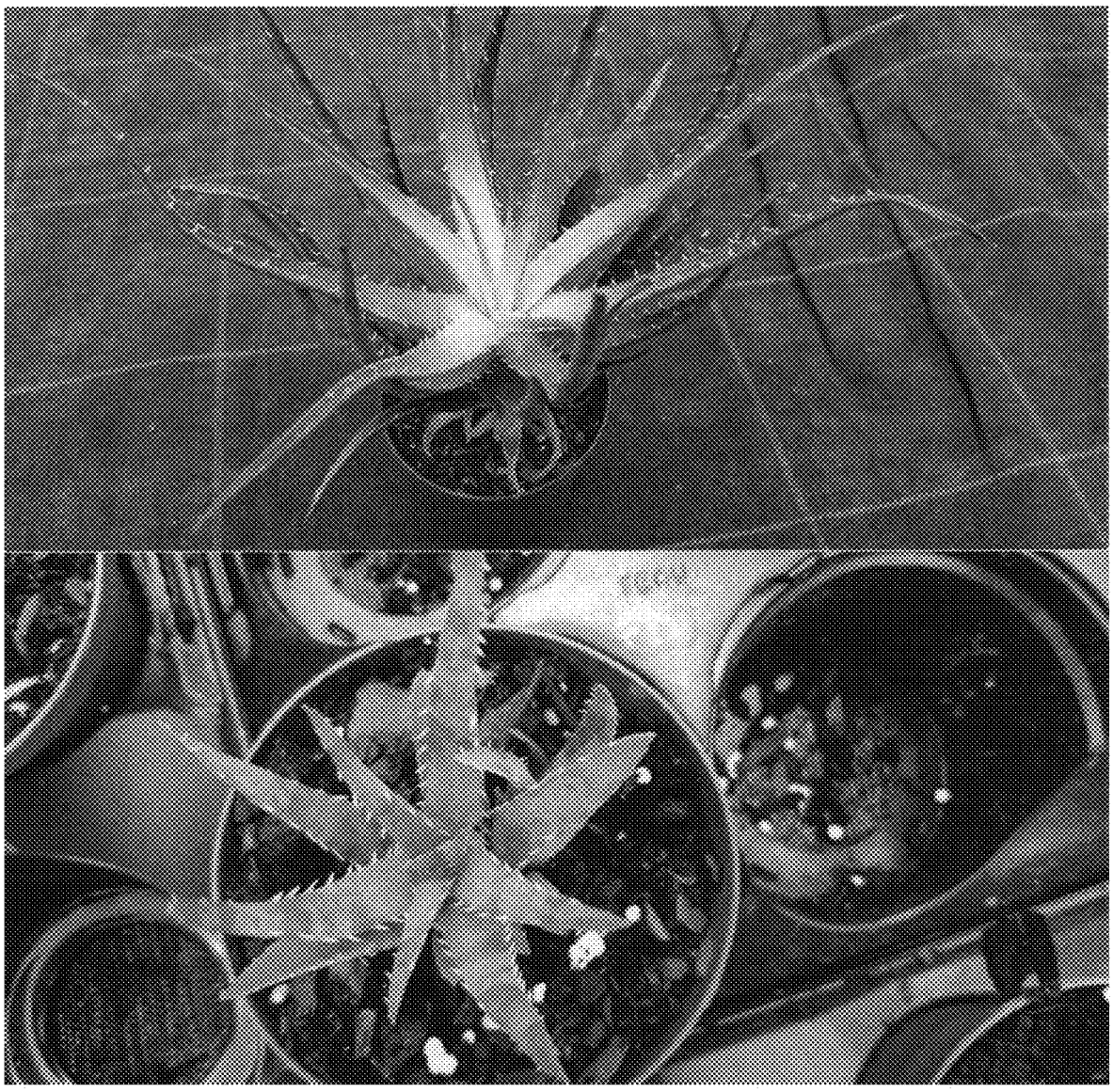

FIG. 4. shows a top view comparison of the central rosette of 'BAGCO01' (top) with the central rosette of the unnamed progenitor *Aloe* x *humilis* plant (bottom).

DESCRIPTION OF THE NEW VARIETY

In the following description, color references are made to The Royal Horticultural Society Colour Chart, Sixth Edition, except where general terms of ordinary dictionary significance are used.

The following observations and measurements describe plants grown in 4-inch round (1-pint) containers when grown in a greenhouse under a natural photoperiod in 72% shade in Zolfo Springs, Fla. Year-round temperatures ranged from approximately 60° to 90° F. during the day and 50° F. to 70° F. at night. Detailed descriptions were taken in July 2019 from approximately 6-month-old plants grown from in-vitro meristem tip cuttings. Measurements and numerical values represent averages of typical plant types.

DETAILED BOTANICAL DESCRIPTION

Classification:

*Botanical name.*—*Aloe* x *humilis.*

*Common name.*—*Aloe.*

*Denomination.*—'BAGCO01'.

Propagation:

*Type.*—Vegetative propagation and in-vitro meristem tip cuttings.

*Time to initiate roots.*—Approximately 2 weeks.

*Time to produce a rooted young plant.*—Approximately 60 days to produce a rooted young plant in a 72-cell pack liner tray.

Plant description:

*Plant type.*—Succulent perennial.

*Growth habit.*—Upright and dwarf, foliage growing in a non-branched basal rosette.

*Suckering habit.*—3 suckers on a 6-month old plant.

*Height from soil to top of foliar plane.*—19.0 cm.

*Plant spread.*—14.0 cm.

*Growth rate.*—Moderate.

*Plant vigor.*—Moderate.

Foliage description:

*Arrangement.*—Simple, arranged in a basal rosette.

*Attachment.*—Sessile.

*Quantity of leaves per rosette.*—Approximately 16.

*Leaf shape.*—Narrowly sublate, elongated.

*Leaf dimensions* (*mature leaf*).—Length: 16.5 cm. Width: 2.0 cm at the base, narrowing to 1.3 cm at the center, narrowing to 0.65 cm when measured 2.5 cm below the apex.

*Leaf blade profile in cross section.*—Flat to slightly concave at the base, becoming more concave from the center to the tip of the leaf blade.

*Leaf attitude.*—45 degrees at attachment to main stem, then becoming more upright through the center of the leaf; on some leaves, the last 5.0 cm to 7.0 cm of leaf tip curve slightly outwards.

*Leaf apex.*—Acuminate.

*Leaf base.*—Rounded, decurrent.

*Leaf margins.*—Slightly revolute, denticulate. Teeth: An average of 35 to 40 teeth per leaf; teeth measure 0.318 cm in length and are spaced apart at a distance of approximately 0.635 cm on a mature leaf; teeth are colored RHS NN155D (yellowish white) on a mature leaf.

*Leaf texture* (*both adaxial and abaxial surfaces*).—Glabrous.

*Leaf luster* (*both adaxial and abaxial surfaces*).—Matte.

*Leaf surface* (*adaxial*).—Finely pubescent.

*Leaf color.*—Juvenile foliage: Adaxial surface: Mostly RHS 1C (light greenish yellow) with slight RHS 189B (pale green) at the apex. Abaxial surface: Mostly RHS 1C (light greenish yellow) with slight RHS 189B (pale green) at the apex. Mature foliage: Adaxial surface: RHS 1C (light greenish yellow) at the base with striping of RHS N189A (dark greyish green) diffused with RHS 189B (pale green) before turning solid RHS N189A (dark greyish green) through the center and out towards the apex, striping fades with age. Abaxial surface: RHS N189C (pale green) with blotchy mottling of RHS 1C (light greenish yellow) at the base and near the center of the leaf blade.

Inflorescence: Flowers have not been observed.

Disease and pest tolerance: None observed.

COMPARISON WITH PARENT VARIETY

'BAGCO01' differs from the progenitor *Aloe* x *humilis* plant (unpatented) in that 'BAGCO01' has juvenile and mature foliage leaf bases colored RHC 1C, whereas juvenile and mature foliage leaf bases of the progenitor *Aloe* x *humilis* plant are colored a solid RHS 189C.

I claim:

1. A new and distinct variety of *Aloe* plant named 'BAGCO01', substantially as illustrated and described herein.

* * * * *